(12) United States Patent
Pribil et al.

(10) Patent No.: US 7,768,660 B1
(45) Date of Patent: *Aug. 3, 2010

(54) NON-DESTRUCTIVE APPROACH TO ELLIPSOMETRIC MONITORING OF A FILM COATING ON THE INNER SURFACE OF A TUBE SHAPED SAMPLE

(75) Inventors: Gregory K. Pribil, Lincoln, NE (US); John A. Woollam, Lincoln, NE (US); Martin M. Liphardt, Lincoln, NE (US); James D. Welch, Omaha, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 503 days.

This patent is subject to a terminal disclaimer.

(21) Appl. No.: 11/897,401

(22) Filed: Aug. 30, 2007

Related U.S. Application Data

(63) Continuation-in-part of application No. 11/288,785, filed on Nov. 30, 2005, now Pat. No. 7,385,698, which is a continuation-in-part of application No. 11/098,669, filed on Apr. 2, 2005, now Pat. No. 7,239,391, and a continuation-in-part of application No. 10/238,241, filed on Sep. 10, 2002, now Pat. No. 6,937,341, and a continuation-in-part of application No. 10/194,881, filed on Jul. 15, 2002, now Pat. No. 6,940,595, and a continuation-in-part of application No. 09/916,836, filed on Jul. 27, 2001, now Pat. No. 6,636,309, and a continuation-in-part of application No. 09/756,515, filed on Jan. 9, 2001, now Pat. No. 6,455,853.

(60) Provisional application No. 60/842,456, filed on Sep. 6, 2006, provisional application No. 60/639,097, filed on Dec. 27, 2004.

(51) Int. Cl.
*G01J 4/00* (2006.01)

(52) U.S. Cl. .................. 356/639; 356/237.1; 356/364; 356/369; 356/451

(58) Field of Classification Search ... 356/237.1–237.6, 356/364–369, 451
See application file for complete search history.

(56) References Cited

U.S. PATENT DOCUMENTS

| | | | |
|---|---|---|---|
| 3,799,679 A | 3/1974 | Simko | 356/200 |
| 6,088,092 A | 7/2000 | Chen et al. | 356/237.2 |
| 6,088,104 A | 7/2000 | Peterson | 356/371 |
| 6,097,482 A | 8/2000 | Smith et al. | 356/237.1 |
| 6,130,749 A | 10/2000 | Meeks et al. | 356/381 |
| 6,166,808 A | 12/2000 | Greve | 356/375 |
| 6,198,533 B1 | 3/2001 | Meeks et al. | 356/381 |
| 6,392,749 B1 | 5/2002 | Meeks et al. | 356/381 |
| 7,385,698 B1 * | 6/2008 | Welch et al. | 356/369 |
| 2002/0113200 A1 | 8/2002 | Hajjar et al. | |

* cited by examiner

*Primary Examiner*—Gregory J Toatley, Jr.
*Assistant Examiner*—Iyabo S Alli
(74) *Attorney, Agent, or Firm*—James D. Welch

(57) ABSTRACT

Disclosed is the use of a focused electromagnetic beam which is caused to impinge on the top surface of a tube shaped sample, to investigate a film coating on its inner surface during fabrication thereof and/or thereafter.

23 Claims, 4 Drawing Sheets

US 7,768,660 B1

NON-DESTRUCTIVE APPROACH TO ELLIPSOMETRIC MONITORING OF A FILM COATING ON THE INNER SURFACE OF A TUBE SHAPED SAMPLE

This Application directly Claims Benefit of Provisional Application Ser. No. 60/842,456 Filed Sep. 6, 2006. This Application is also a CIP of application Ser. No. 11/288,785 Filed Nov. 30, 2005 now U.S. Pat. No. 7,385,698 and therevia of Ser. No. 11/098,669 Filed Apr. 2, 2005 now U.S. Pat. No. 7,239,391 and therevia of Ser. No. 10/238,241 Filed Sep. 10, 2002 now U.S. Pat. No. 6,937,341 and therevia of Ser. No. 09/756,515 Filed Jan. 9, 2001, (now U.S. Pat. No. 6,455,853). Further this Application is a CIP of Ser. No. 10/194,881 Filed Jul. 15, 2002 now U.S. Pat. No. 6,940,595 and therevia of Ser. No. 09/916,836 Filed Jul. 27, 2001, (now U.S. Pat. No. 6,636,309). This Application also Claims Benefit of Provisional Application Ser. No. 60/639,097 Filed Dec. 27, 2004.

TECHNICAL FIELD

The present invention relates to the ellipsometric investigation of films beneath a top surface of a sample, and more particularly to the use of a focused electromagnetic beam which is caused to impinge on the top surface of a tube shaped sample, to investigate a film coating on its inner surface during fabrication thereof and/or thereafter.

BACKGROUND

Generally, a problem inherent in monitoring electromagnetic radiation which is reflected from a sample outer surface is that it often is contaminated with reflections from a backside thereof. One approach to preventing this problem is to roughen the backside. Another is to place a mask on the surface of the sample which allows surface reflections to proceed, but prevents backside reflections from exiting. Another approach yet is to place a blocking means between the sample and the detector which blocks backside reflections but lets front surface reflections proceed into the detector. Said approaches, however, do not allow for selectively monitoring electromagnetic radiation reflected from the front or backside. In that light it is noted that backside reflected electromagnetic energy contains information which is different from that contained in outer surface reflections.

Continuing, it is also disclosed that ellipsometry monitors the product of refractive index and thickness in samples investigated thereby, and that said parameters are correlated in what can be termed an optical thickness. A known approach to breaking the correlation is to obtain data from two samples comprising the same material(s) but which samples are of different thicknesses. Simultaneously regression of the data obtained from both sides onto corresponding mathematical models leads to substantially uncorrelated evaluation of refractive index and thicknesses.

It is also mentioned that it is known to obtain data from front and backsides of a sample and simultaneously regress said data onto a mathematical model therefore.

More on-point as regards the present invention, it is known to cause a polarized electromagnetic beam to impinge on the top surface of a sample along with monitoring reflected electromagnetic radiation therefrom to enable characterization of the sample as a composite. The detected reflected electromagnetic radiation generally includes interfering components which reflect from said top surface and from various interfaces between a plurality of layers.

It is also known to focus electromagnetic radiation onto a surface of a sample (e.g. 25 micron spot size), comprised of a front and back, and that electromagnetic radiation reflected from the front and back can become spatially separated from one another when such focusing is utilized. This avoids the complication of interference effects between various components reflected from different interface locations in the sample, by allowing separate monitoring of the various reflections. That is, the electromagnetic radiation reflected from a coating on the bottom of a sample can be monitored substantially free of components reflected from the top surface and various intervening interfaces.

further, it is known that appropriate orientation of an impinging beam of electromagnetic with respect to a curved sample surface can make the curved surface appear essentially as a flat surface, (e.g. align the beam orientation with a longitudinal dimension of a cylinder), to an electromagnetic beam of small diameter.

In addition, a Co-Pending patent application Ser. No. 11/288,785 it is disclosed to use a detector to selectively intercept portions of a focused beam caused to impinge on a sample comprising a top surface and at least one interface therebelow.

Known Patents and Published Applications are:

Patent Application No. 2002/0113200 A1 was identified as an aperture 103A is disclosed which can be placed near a detector to block entry of one of two beams from different sources.

U.S. Pat. No. 3,799,679 to Simko is disclosed as an iris (38) is present near a detector which can be adjusted to block entry of backside reflection thereinto.

Patents to Meeks, U.S. Pat. Nos. 6,130,749, 6,198,533 and 6,392,749 are disclosed for the presence of a hole 2022 in an integrating sphere near, but not atop a sample.

U.S. Pat. No. 6,088,092 to Chen et al. is disclosed as it applies a spatial filter (28) to block backside reflection entry into a detector.

U.S. Pat. No. 6,088,104 to Peterson is disclosed as a blocking element (B) is present which can be used to block electromagnetic radiation entry to a detector.

U.S. Pat. No. 6,097,482 to Smith et al. is disclosed as it applies baffles to block light entry to a detector.

U.S. Pat. No. 6,166,808 to Greve is disclosed as it describes use of an aperture near a detector to block backside reflections entry to a detector.

U.S. Pat. No. 5,936,734 is identified as it describes a method of partitioning electromagnetic radiation into coherent and incoherent portions when calculating intensity.

U.S. Pat. No. 6,455,853 to Herzinger at al. is identified as it describes obtaining data from both sides of a sample.

The various known factors recited above however, have not, to the Applicant's knowledge, been combined to provide a non-destructive method of characterizing a thin film coating present on the inner surface of a tube shaped sample. Need remains for a system and non-destructive method which allows investigation of a film present on an inner surface of a tube shaped sample.

DISCLOSURE OF THE INVENTION

When faced with characterizing, for instance, the optical constants and/or thickness of a thin film present on the inner surface of a tube shaped sample, an obvious approach is to obtain a broken piece thereof and use conventional ellipsometry methodology to directly apply a polarized electromagnetic beam to said thin film coating. A strong reflection from the surface of such a film can be analyzed conventionally with good results being achieved. This approach is fine where, say, broken pieces of the tube are available, but does not work in a setting where, for instance, the tube can not be broken in order to provide such direct access to the coating on said inner surface. This can, for instance, occur during manufacture fabrication of a tube which has a coating on the inner surface thereof and it is desired to monitor the fabrication results in real time.

The present invention, in a preferred mode of operation applies focused beam electromagnetic radiation to the top surface of a tube shaped sample, in combination with the detection of a component of said electromagnetic beam which is reflected from an interface between the inner surface of said tube and a thin coating thereon. Use of a focused beam applied at an oblique angle and preferably in a direction aligned along the longitudinal dimension of the tube shaped sample, (to best approximate incidence on a flat sample surface), results in separately detectable reflections from the top surface (i.e. the outer surface of said tube shaped system), and from the interface between the inner surface thereof and the film coating thereupon. Analysis of said separately detected reflected electromagnetic radiation from the interface between the inner surface thereof and the film coating thereupon allows determining optical constants and/or thickness of said film coating.

It is noted that the beam can be directed to approach the tube shaped sample in a direction coincident with its small lateral dimension, but this can cause the beam to impinge on a surface which does not best approximate a flat sample surface, thus directing the beam along the major dimension of the tube is preferred.

A present invention system is then sequentially comprised of:
 a source of electromagnetic radiation;
 a tube shaped sample having a outer surface and having a film coating present on an inner surface thereof; and
 a detector;

said source, sample and detector being oriented such that electromagnetic radiation from said source is directed at said sample outer surface at an oblique angle, reflects therefrom and enters said detector, said detector being of a small dimension as compared to the spread between reflection from said sample outer surface and reflection from an interface between said tube shaped sample and the film coating on said inner surface thereof, said detector being capable of selective monitoring of electromagnetic radiation reflected from the outer surface or from said interface between said tube shaped sample and the film coating on said inner surface thereof.

Said system can further comprise providing at least one selection from the group consisting of:
 a polarizer means between said source and sample;
 an analyzer means between said sample and detector;
 at least one compensator between said source and detector; and
 at least one focusing element positioned such that electromagnetic radiation from said source is directed at said sample at a plurality of oblique angles.

The system provided can then be a reflectometer, spectrophotometer, ellipsometer or ellipsometer or the like.

A method of non-destructively investigating properties of a film coating present on an inner surface of a tube shaped system during fabrication thereof or thereafter, comprises the steps of:

practicing steps a and b simultaneously or in either order;

a) providing a tube shaped sample comprising outer and inner surfaces, said tube shaped sample having a film coating present on its inner surface;
 b) providing a system for causing a focused beam of electromagnetic radiation to impinge upon the outer surface of said tube shaped system at an oblique angle of incidence, and a detector situated to receive a component thereof reflected from the interface between said inner surface of said tube shaped sample and said film coating present thereupon;
 c) collecting and analyzing said electromagnetic radiation reflected from the interface between said inner surface of said tube shaped sample and said film coating present thereupon, to determine the optical constants and/or thickness of said film coating.

Another method of selectively monitoring reflections from a sample during fabrication thereof or thereafter, comprises the steps of:
 a) providing a system which is sequentially comprised of:
  a source of electromagnetic radiation,
  a tube shaped sample having an outer surface and an inner surface with a film coating present thereon, and
  a detector;

said source, sample and detector being oriented such that electromagnetic radiation from said source is directed at said sample at an oblique angle, reflects therefrom and enters said detector, said detector being of a small dimension as compared to the spread between reflection from said sample outer surface and reflection from an interface between said tube shaped sample and the film coating on said inner surface thereof, said sample and/or detector being mounted to allow movement thereof so that said detector can intercept electromagnetic radiation reflected from the outer surface or said interface between said tube shaped sample and the film coating on said inner surface;
 b) causing a beam of electromagnetic radiation to reflect from said sample; and
 c) moving at least one selection from the group consisting of:
  said detector; and
  said tube shaped sample;

such that electromagnetic radiation reflects from the sample outer surface or from the interface sample between said tube shaped sample and the film coating on said inner surface thereof.

A method of selectively monitoring outer surface or interface reflections from a sample, or transmission therethrough during fabrication thereof or thereafter, comprises the steps of:
 a) providing a system which is sequentially comprised of:
  a source of electromagnetic radiation,
  a tube shaped sample having a outer surface and having a film coating present on an inner surface thereof, and
  a detector;

said source, sample and detector being oriented such that electromagnetic radiation from said source is directed at said sample at an oblique angle, reflects therefrom or transmits therethrough and enters said detector, said detector being of a small dimension as compared to the spread between reflection from said sample outer surface and reflection from an interface between said tube shaped sample and the film coating on said inner surface thereof, and therefore, being capable of selective monitoring of electromagnetic radiation reflected from the outer surface or from said interface between said tube shaped sample and the film coating on said inner surface thereof;

b) causing a beam of electromagnetic radiation to at least partially reflect from said sample at an oblique angle; and c) causing said detector to selectively monitor electromagnetic radiation reflected from the sample outer surface or from the interface between said tube shaped sample and the film coating on said inner surface or which is transmitted through said sample and obtaining data;

Another method of pursuing uncorrelated determination of refractive index and thickness of a film on an inner surface of a tube shaped sample during fabrication thereof or thereafter, comprises:

practicing steps a and a' sequentially or simultaneously in either order:
    a) providing a system which is sequentially comprised of:
    a source of electromagnetic radiation;
    a tube shaped sample having outer surface and a film coating present on an inner surface thereof;

and
    at least one detector that allows selective
    monitoring at least two selections from the group consisting of:
        reflection from the outer surface;
        reflection from an interface between said tube shaped sample and said
            film coating present on said inner surface thereof, and
        transmission through the film coating present on the inner surface thereof;

independently;

said detector(s) being selected from the group consisting of:
    comprising a fixed location detector;
    comprising a plurality of substantially fixed location detector elements;
    comprising a movable detector element; and
    comprising a detector element accessed by a movable optical fiber;

said source, sample and detector being oriented such that electromagnetic radiation from said source is directed at said sample at an oblique angle;
    a') providing a mathematical model of said sample;
    b) causing a beam of electromagnetic radiation to impinge onto said sample at an oblique angle of incidence; and
    c) independently monitoring at least two selections form the group consisting of:
        reflection from the outer surface;
        reflection from the interface between said tube shaped sample and said
            film coating present on the inner surface thereof; and
        transmission through said film;
    d) simultaneously regressing at least two monitored data sets obtained in step c onto said mathematical model provided in step a'.

Any of the foregoing methodology can involve analysis of the reflections from the outer surface and said interface between said tube shaped sample and the film coating on said inner surface thereof are analyzed separately with the reflection from the outer surface providing information about the surface region of the sample and the reflection from the interface between said tube shaped sample and the film coating on said inner surface thereof providing information about the film.

It is mentioned for emphasis that the foregoing methods preferably involve providing a focusing element in the oblique angle of incidence incident beam, and that said focusing element can comprise refractive or reflective components, or a combination of refractive and reflective components.

Any of the foregoing methods can further comprise performing at least one selection from the group consisting of:
    storing at least some data provided by said data detector in machine readable media;
        analyzing at least some of the data provided by said detector and storing at least some of the results of said analysis in machine readable media;
        displaying at least some data provided by said detector by electronic and/or non-electronic means;
        analyzing at least some of the data provided by said detector and displaying at least some of the results of said analysis by electronic and/or non-electronic means;
        causing at least some data provided by said detector to produce a signal which is applied to provide a concrete and tangible result;
        analyzing at least some of the data provided by said detector and causing at least some thereof to produce a signal which is applied to provide a concrete and tangible result.

In any of the foregoing Methods the step of providing a system further can involve providing at least one selection from the group consisting of:
    a polarizer means between said source and sample;
    an analyzer means between said sample and detector;
    at least one compensator between said source and detector; and
    at least one focusing element positioned such that electromagnetic radiation from said source is directed at said sample at a plurality of an oblique angles.

The systems provided in any of the Methods can be a reflectometer, spectrophotometer, ellipsometer or ellipsometer or the like.

Any of the recited methods can further comprises a selection from the group consisting of:
    rotating; and
    translating;

continuously or step-wise, said tube shaped sample during data collection. This enables collecting data to investigate the uniformity of the film coating present on said inner surface of the tube.

It is specifically noted that a present invention system can comprise any combination of movable or fixed location tube shaped sample and movable or fixed location detector. such as:
    a movable tube shaped sample and a fixed location detector;
    a movable tube shaped sample and a movable detector;
    a fixed location tube shaped sample and a movable detector;

such that in use a reflected component of an incident focused oblique angle of incidence beam can be caused to enter a detector or detector element by motion of one or both of the tube shaped sample and/or detector.

In addition, it is noted that the terminology "a focusing element positioned such that electromagnetic radiation from said source is directed at said sample at a plurality of an oblique angles", means that a range of angles of incidence around the beam oblique angle of incidence is effected by the focusing element.

Finally, it is specifically noted that the present invention can be practiced during the fabrication thereof as the film on the inner surface of said tube shaped sample is deposited or otherwise applied, or during post fabrication investigation.

The present invention will be better understood by reference to the Detailed description Section of this Specification, in combination with the Drawings.

DETAILED DESCRIPTION

Figure 1:
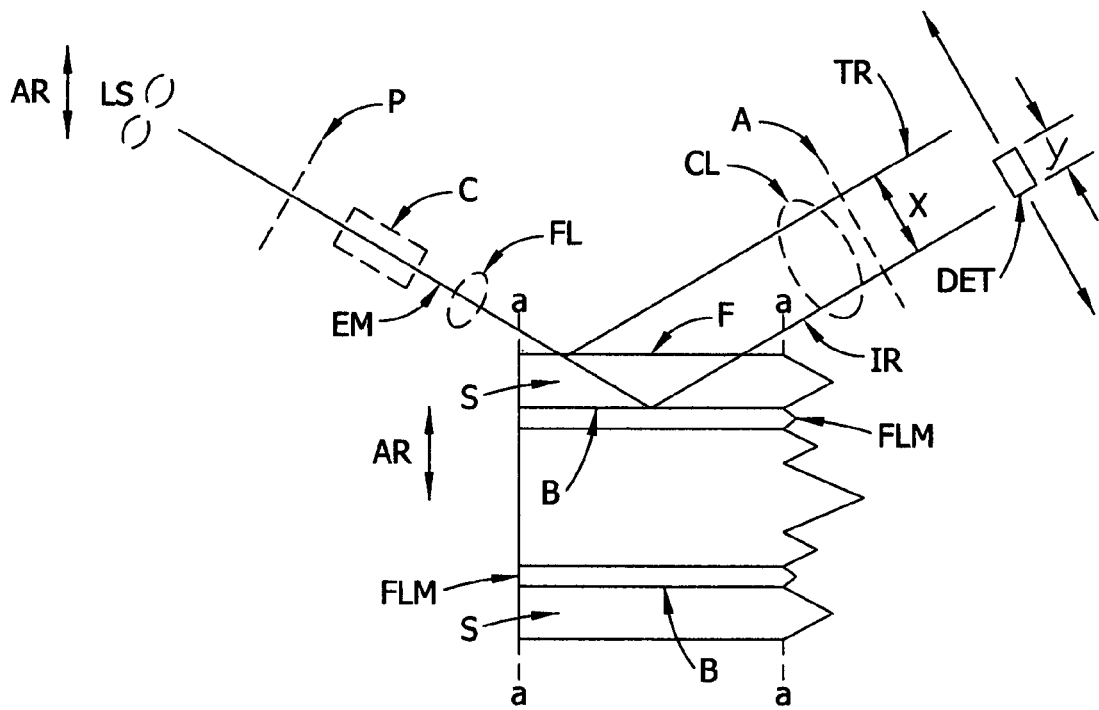
FIG. 1 demonstrates a partial length of a Cross-Section of a Tube shaped sample and that a reflected focused beam of electromagnetic radiation caused to impinge on a sample at an oblique angle of incidence can be separated into components reflected from the top (TR) and back (IR) sides thereof.
Figure 2:
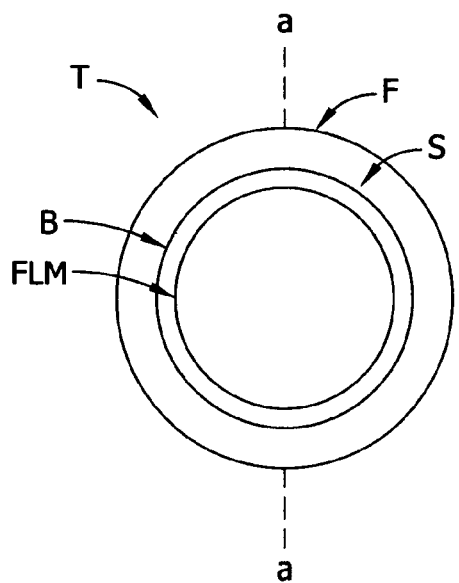
FIG. 2 shows an end view of the Tube shaped sample shown in FIG. 1, with indication a-a of where the FIG. 1 Cross-Section is taken thereon.

FIG. 1 shows a partial length of a Tube Shaped Sample (T) taken in Cross-Section at a-a in an end view thereof as shown in FIG. 2.

FIG. 1 further demonstrates reflected components (IR) and (TR) of a focused beam (EM) of electromagnetic which is caused to impinge on the outer Surface (F) of a Tube Shaped Sample (T) at an oblique angle of incidence. Note that the Wall of the Tube (T) Shape Sample is identified as (S) and said Sample (T) is drawn to imply similarity of said Wall (S) to a flat-substrate type sample when the Beam (EM) approaches in a direction coincident with the longitudinal dimension of the Tube Shaped Sample (T) as shown. Shown also are a Source (LS) of electromagnetic radiation, a Polarizer (P), an optional Compensator (C), a Focusing Element (FL), and a Detector (DET) which can be positioned to selectively intercept a component thereof reflected from the Front (F) or Back (B) surface of said Wall (S). Note interface between said Inner Surface of said Tube Shaped Sample (T) and said film coating (FLM) present thereupon at the Back (B) surface of the Wall (S). The Sample is shown in cross-section and indicated as being Tube Shaped by inclusion of the lower portion thereof.

It is mentioned that while it is shown to move the Detector (DET) to selectively intercept various components of the Reflected Electromagnetic Beam, (e.g. the reflection from the Top Surface (TR) or the Interface (IR)), it is also possible to alternatively or in addition to, move the Sample (T) and/or Electromagnetic Beam (EM) upward or downward. See arrows (AR) in FIG. 1 which indicate such possibility.

It is also noted that continuous or step-wise rotation of the Tube Shaped Sample (T) as it is viewed in FIG. 2, and/or continuous or stepwise translation thereof, to the right or left, as viewed in FIG. 1 allows collecting data which can allow determination of film consistency.

Figure 3A:
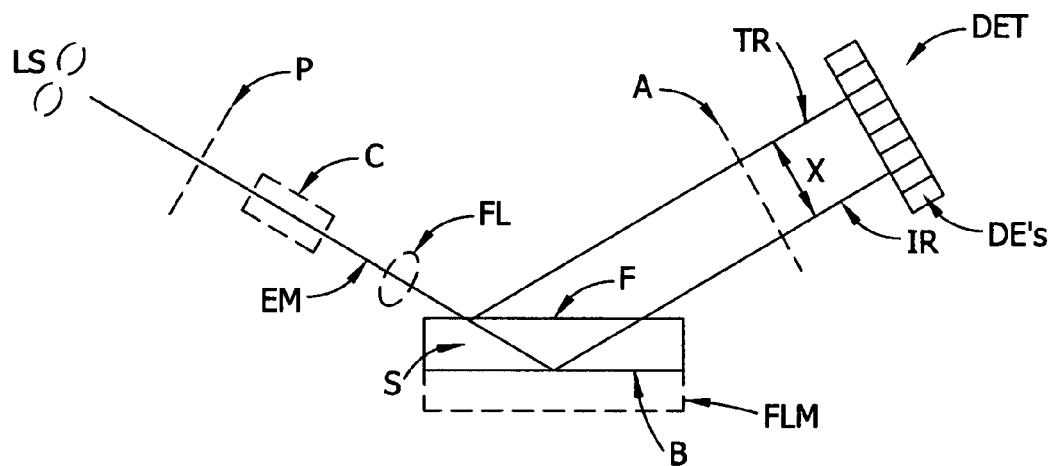
FIG. 3a demonstrates that a detector (DET) can comprise a plurality of detector elements (DE's) and be positioned stationary with respect to reflected beams.
Figure 3B:
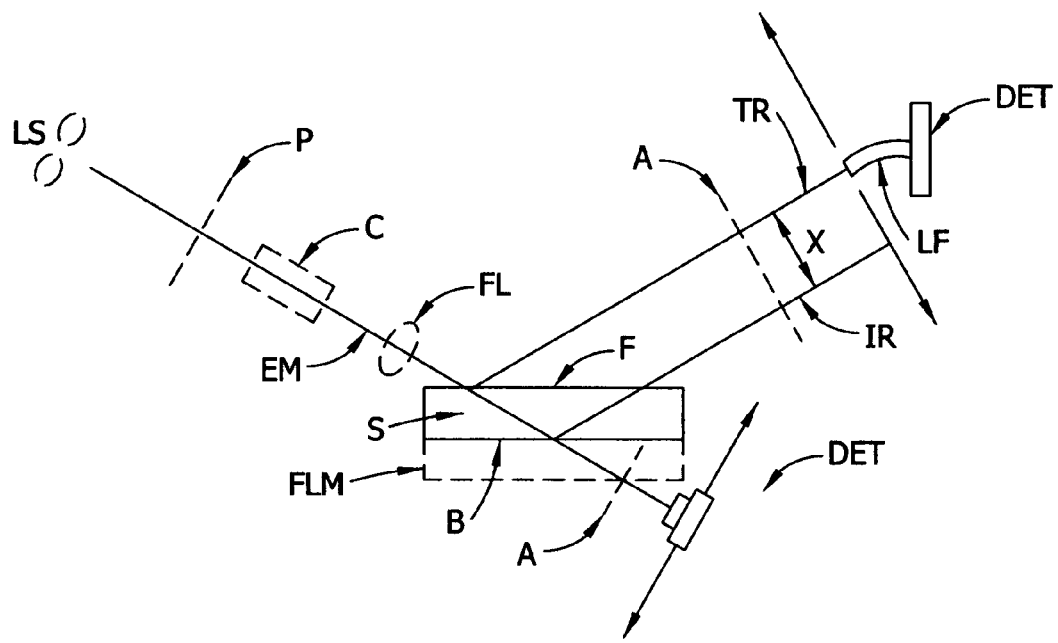
FIG. 3b shows that a detector can be provided signal via a movable light fiber.

Also, while a refractive Focusing Lens (FL) is shown in FIG. 1 it is possible to utilize Reflective Focusing Optics. Any functional Focusing Element is within the scope of the Claims and generally referred to as Focusing Elements, as represented by (FL). Note also that a Collimating Element (CL) can be positioned between the Sample (T) and Detector (DET). Further, said Detector (DET) can comprise a plurality of Detector Elements (DE's) as shown in FIG. 3a, and be positioned stationary with respect to reflected beams (TR) and (IR) so that said (TR) and (IR) enter different Detector Elements (DE's). FIG. 3b shows that a Detector can be provided signal via a movable Light Fiber (LF), and where geometry allows, near the end of a tube, a transmitted signal can be monitored. Again, the Sample (T) could also, or in the alternative, be moved. (Note that only the top of the Tube is shown in FIGS. 3a and 3b).

Figure 4:
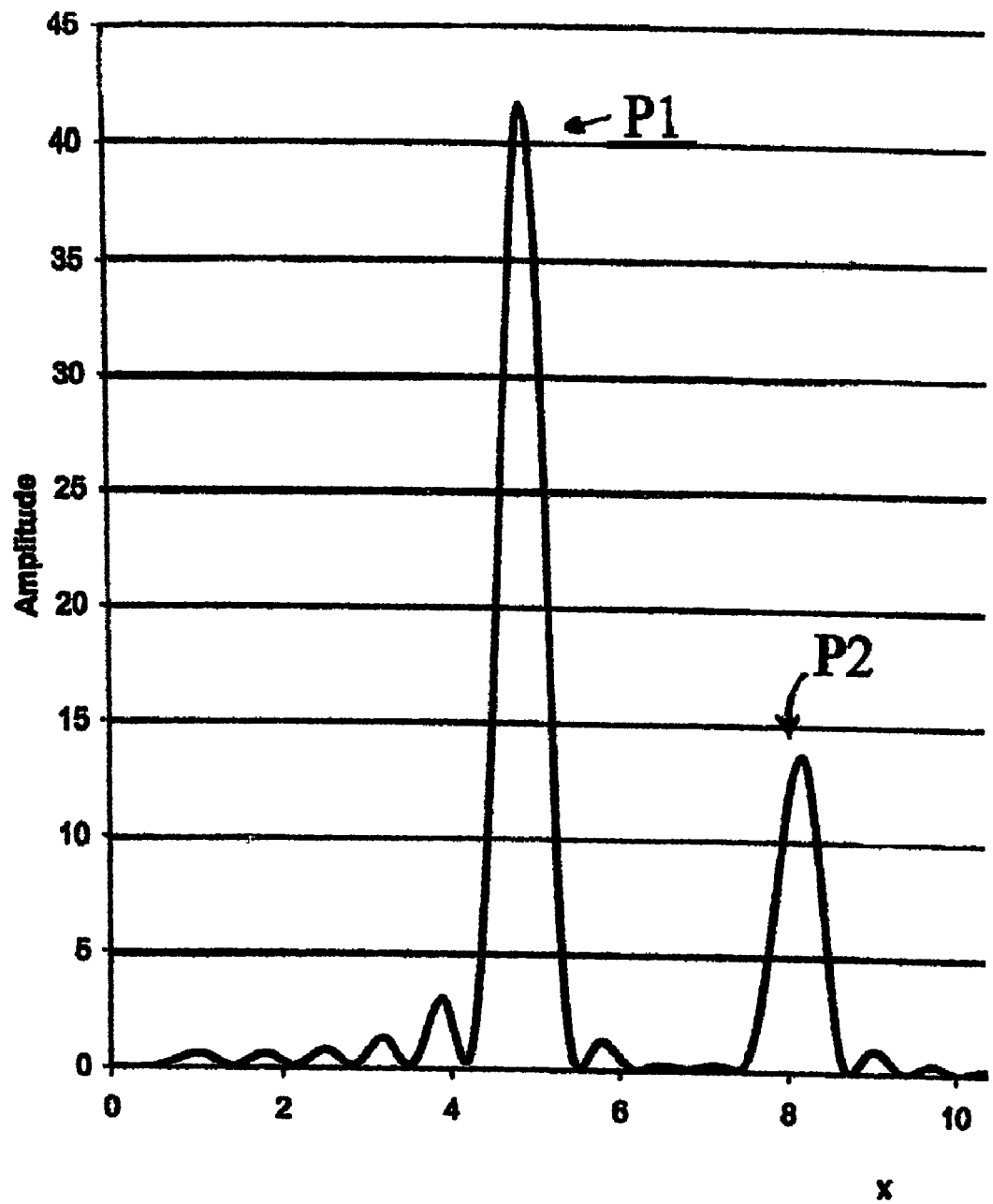
FIG. 4 shows how reflections (P1) and (P2) of a focused beam, which are from a top and from an interface, as shown in FIGS. 1, 3a and 3b are separated in space.

FIG. 4 shows how reflections (P1) and (P2) of a focused beam, which are from a top surface and from an interface and reflect as (TR) and (IR) respectively, as shown in FIGS. 1, 3a and 3b are separated in space.

Figure 5:
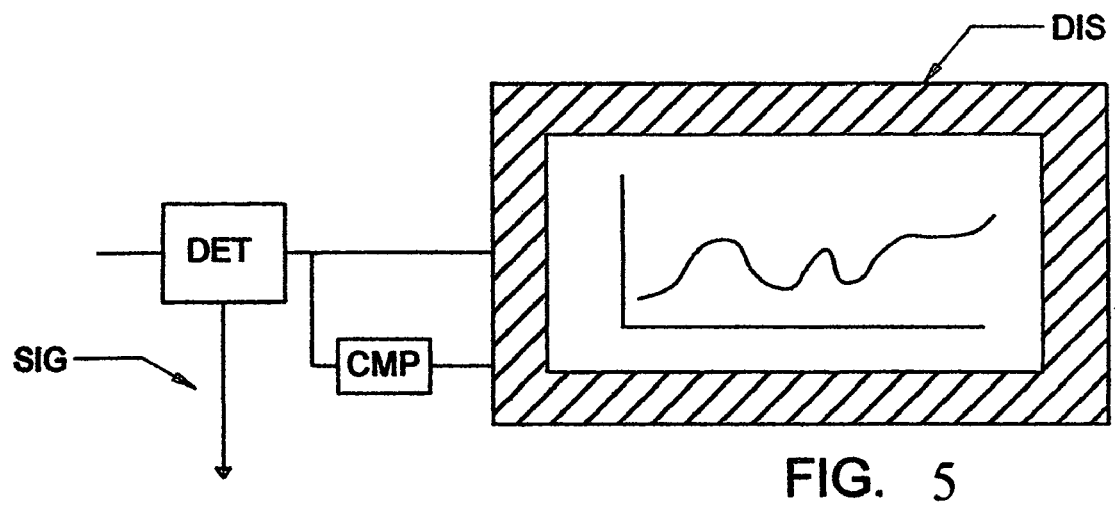
FIG. 5 demonstrates signals developed by practice of the present invention can be used and/or displayed.

FIG. 5 demonstrates signals developed by practice of the present invention can be used to provide a concrete and tangible result and/or can be displayed etc.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of non-destructively investigating properties of a film coating being formed on, or present on an inner surface of a tube shaped system comprising the steps of:
   practicing steps a and b simultaneously or in either order;
   a) providing a tube shaped sample comprising outer and inner surfaces, said tube shaped sample having a film coating present on its inner surface;
   b) providing a system for causing a beam of electromagnetic radiation to impinge upon the outer surface of said tube shaped system at an oblique angle of incidence, and a detector situated to receive a component thereof reflected from the interface between said inner surface of said tube shaped sample and said film coating present thereupon;
   c) collecting and analyzing said electromagnetic radiation reflected from the interface between said inner surface of said tube shaped sample and said film coating present thereupon, to determine the optical constants and/or thickness of said film coating;
   said method further comprising performing at least one selection from the group consisting of:
   storing at least some data provided by said data detector in machine readable media;
   analyzing at least some of the data provided by said detector and storing at least some of the results of said analysis in machine readable media;
   displaying at least some data provided by said detector by electronic and/or non-electronic means;
   analyzing at least some of the data provided by said detector and displaying at least some of the results of said analysis by electronic and/or non-electronic means;
   causing at least some data provided by said detector to produce a signal which is applied to provide a concrete and tangible result;
   analyzing at least some of the data provided by said detector and causing at least some thereof to produce a signal which is applied to provide a concrete and tangible result.

2. A method, incorporating by reference the limitations in claim 1, in which the step of providing a system further comprises providing at least one selection from the group consisting of:
- a polarizer means between said source and sample;
- an analyzer means between said sample and detector;
- at least one compensator between said source and detector; and
- at least one focusing element positioned such that electromagnetic radiation from said source is directed at said sample at a plurality of an oblique angles.

3. A method of selectively monitoring reflections from a sample, comprising the steps of:
   a) providing a system which is sequentially comprised of: a source of electromagnetic radiation, a tube shaped sample having an outer surface and an inner surface with a film coating present thereon, and a detector; said source, sample and detector being oriented such that electromagnetic radiation from said source is directed at said sample at an oblique angle, reflects therefrom and enters said detector, said detector being of a small dimension as compared to the spread between reflection from said sample outer surface and reflection from an interface between said tube shaped sample and the film coating on said inner surface thereof, said sample and/or detector being mounted to allow movement thereof so that said detector can intercept electromagnetic radiation reflected from the outer surface or said interface between said tube shaped sample and the film coating on said inner surface;
   b) causing a beam of electromagnetic radiation to reflect from said sample; and
   c) moving at least one selection from the group consisting of:
   - said detector; and
   - said tube shaped sample;

such that electromagnetic radiation is reflected from the sample outer surface or from the interface sample between said tube shaped sample and the film coating on said inner surface thereof and into said detector;
said method further comprising performing of at least one selection from the group consisting of:
- storing at least some data provided by said data detector in machine readable media;
- analyzing at least some of the data provided by said detector and storing at least some of the results of said analysis in machine readable media;
- displaying at least some data provided by said detector by electronic and/or non-electronic means;
- analyzing at least some of the data provided by said detector and displaying at least some of the results of said analysis by electronic and/or non-electronic means;
- causing at least some data provided by said detector to produce a signal which is applied to provide a concrete and tangible result;
- analyzing at least some of the data provided by said detector and causing at least some thereof to produce a signal which is applied to provide a concrete and tangible result.

4. A method, incorporating by reference the limitations in claim 3, in which the step of providing a system further comprises providing at least one selection from the group consisting of:
- a polarizer means between said source and sample;
- an analyzer means between said sample and detector;
- at least one compensator between said source and detector; and
- at least one focusing element positioned such that electromagnetic radiation from said source is directed at said sample at a plurality of an oblique angles.

5. A system which is sequentially comprised of:
- a source of electromagnetic radiation;
- a tube shaped sample having a outer surface and having a film coating present on an inner surface thereof; and
- a detector;

said source, sample and detector being oriented such that electromagnetic radiation from said source is directed at said sample outer surface at an oblique angle, reflects therefrom and enters said detector, said detector being of a small dimension as compared to the spread between reflection from said sample outer surface and reflection from an interface between said tube shaped sample and the film coating on said inner surface thereof, said detector being capable of selective monitoring of electromagnetic radiation reflected from the outer surface or from said interface between said tube shaped sample and the film coating on said inner surface thereof.

6. A system, incorporating by reference the limitations in claim 5, in which said system further comprises providing at least one selection from the group consisting of:
- a polarizer means between said source and sample;
- an analyzer means between said sample and detector;
- at least one compensator between said source and detector; and
- at least one focusing element positioned such that electromagnetic radiation from said source is directed at said sample at a plurality of oblique angles.

7. A method of selectively monitoring outer surface or interface reflections from a sample, or transmission therethrough, during or after fabrication thereof, comprising the steps of:
   a) providing a system which is sequentially comprised of:
   - a source of electromagnetic radiation,
   - a tube shaped sample having a outer surface and having a film coating present on an inner surface thereof, and
   - a detector;

said source, sample and detector being oriented such that electromagnetic radiation from said source is directed at said sample at an oblique angle, reflects therefrom or transmits therethrough and enters said detector, said detector being of a small dimension as compared to the spread between reflection from said sample outer surface and reflection from an interface between said tube shaped sample and the film coating on said inner surface thereof, and therefore being capable of selective monitoring of electromagnetic radiation reflected from the outer surface or from said interface between said tube shaped sample and the film coating on said inner surface thereof;
   b) causing a beam of electromagnetic radiation to at least partially reflect from said sample at an oblique angle; and
   c) causing said detector to selectively monitor electromagnetic radiation reflected from the sample outer surface or from the interface between said tube shaped sample and the film coating on said inner surface or which is transmitted through said sample and obtaining data;

said method further comprising performing at least one selection from the group consisting of:
- storing at least some data provided by said data detector in machine readable media;
- analyzing at least some of the data provided by said detector and storing at least some of the results of said analysis in machine readable media;
- displaying at least some data provided by said detector by electronic and/or non-electronic means;

analyzing at least some of the data provided by said detector and displaying at least some of the results of said analysis by electronic and/or non-electronic means;

causing at least some data provided by said detector to produce a signal which is applied to provide a concrete and tangible result;

analyzing at least some of the data provided by said detector and causing at least some thereof to produce a signal which is applied to provide a concrete and tangible result.

8. A method, incorporating by reference the limitations in claim 7, in which the step of providing a system further comprises providing at least one selection from the group consisting of:

a polarizer means between said source and sample;

an analyzer means between said sample and detector;

at least one compensator between said source and detector; and at least one focusing element positioned such that electromagnetic radiation from said source is directed at said sample at a plurality of oblique angles.

9. A method, incorporating by reference the limitations in claim 2, in which the system provided is a reflectometer, spectrophotometer, ellipsometer polarimeter.

10. A method, incorporating by reference the limitations in claim 4, in which the system comprises a reflectometer, spectrophotometer, ellipsometer, polarimeter.

11. A system, incorporating by reference the limitations in claim 6, which comprises a reflectometer, spectrophotometer, ellipsometer, polarimeter.

12. A method, incorporating by reference the limitations in claim 8, in which the system provided is a reflectometer, spectrophotometer, ellipsometer, polarimeter.

13. A method of pursuing uncorrelated determination of refractive index and thickness of a film on an inner surface of a tube shaped sample during fabrication thereof or thereafter, comprising:

practicing steps a and a' sequentially or simultaneously in either order:

a) providing a system which is sequentially comprised of:

a source of electromagnetic radiation;

a tube shaped sample having outer surface and a film coating present on an inner surface thereof; and at least one detector that allows selective monitoring at least two selections from the group consisting of:

reflection from the outer surface;

reflection from an interface between said tube shaped sample and said film coating present on said inner surface thereof, and transmission through the film coating present on the inner surface thereof;

independently;

said detector(s) being selected from the group consisting of:

comprising a plurality of substantially fixed location detector elements;

comprising a movable detector element; and comprising a detector element accessed by a movable optical fiber;

said source, sample and detector being oriented such that electromagnetic radiation from said source is directed at said sample at an oblique angle;

a') providing a mathematical model of said sample;

b) causing a beam of electromagnetic radiation to impinge onto said sample at an oblique angle of incidence; and c) independently monitoring at least two selections form the group consisting of:

reflection from the outer surface;

reflection from the interface between said tube shaped sample and said film coating present on the inner surface thereof; and transmission through said film;

d) simultaneously regressing at least two monitored data sets obtained in step c onto said mathematical model provided in step a';

said method further comprising performing at least one selection from the group consisting of:

storing at least some data provided by said data detector in machine readable media;

analyzing at least some of the data provided by said detector and storing at least some of the results of said analysis in machine readable media;

displaying at least some data provided by said detector by electronic and/or non-electronic means;

analyzing at least some of the data provided by said detector and displaying at least some of the results of said analysis by electronic and/or non-electronic means;

causing at least some data provided by said detector to produce a signal which is applied to provide a concrete and tangible result;

analyzing at least some of the data provided by said detector and causing at least some thereof to produce a signal which is applied to provide a concrete and tangible result.

14. A method, incorporating by reference the limitations in claim 13, in which the step of providing a system further comprises providing at least one selection from the group consisting of:

a polarizer means between said source and sample;

an analyzer means between said sample and detector;

at least one compensator between said source and detector; and at least one focusing element positioned such that electromagnetic radiation from said source is directed at said sample at a plurality of oblique angles.

15. A method, incorporating by reference the limitations in claim 14, which the system provided is a reflectometer, spectrophotometer, ellipsometer, polarimeter.

16. A method, incorporating by reference the limitations in claim 1, in which analysis of the reflections from the outer surface and said interface between said tube shaped sample and the film coating on said inner surface thereof are analyzed separately with the reflection from the outer surface providing information about the surface region of the sample and the reflection from the interface between said tube shaped sample and the film coating on said inner surface thereof providing information about the film.

17. A method, incorporating by reference the limitations in claim 3, in which analysis of the reflections from the outer surface and said interface between said tube shaped sample and the film coating on said inner surface thereof are analyzed separately with the reflection from the outer surface providing information about the surface region of the sample and the reflection from the interface between said tube shaped sample and the film coating on said inner surface thereof providing information about the film.

18. A method, incorporating by reference the limitations in claim 7, in which analysis of the reflections from the outer surface and said interface between said tube shaped sample and the film coating on said inner surface thereof are analyzed separately with the reflection from the outer surface providing information about the surface region of the sample and the reflection from the interface between said tube shaped sample and the film coating on said inner surface thereof providing information about the film.

19. A method, incorporating by reference the limitations in claim 13, in which analysis of the reflections from the outer surface and said interface between said tube shaped sample and the film coating on said inner surface thereof are analyzed separately with the reflection from the outer surface providing information about the surface region of the sample and the reflection from the interface between said tube shaped sample and the film coating on said inner surface thereof providing information about the film.

20. A method, incorporating by reference the limitations in claim 1, which further comprises a selection from the group consisting of:
   rotating; and
   translating;
continuously or step-wise, said tube shaped sample during data collection.

21. A method, incorporating by reference the limitations in claim 3 which further comprises a selection from the group consisting of:
   rotating; and
   translating;
said tube shaped sample during data collection.

22. A method, incorporating by reference the limitations in claim 7, which further comprises a selection from the group consisting of:
   rotating; and
   translating;
continuously or step-wise, said tube shaped sample during data collection.

23. A method, incorporating by reference the limitations in claim 13, which further comprises a selection from the group consisting of:
   rotating; and
   translating;
continuously or step-wise, said tube shaped sample during data collection.

* * * * *